US00RE34432E

United States Patent [19]

Bertrand

[11] E Patent Number: Re. 34,432

[45] Reissued Date of Patent: Nov. 2, 1993

[54] POWER CONTROL TECHNIQUE FOR BEAM-TYPE ELECTROSURGICAL UNIT

[75] Inventor: Carol Bertrand, Cambridge, Mass.

[73] Assignee: Birtcher Medical Systems, Inc., Irvine, Calif.

[21] Appl. No.: 841,433

[22] Filed: Feb. 19, 1992

Related U.S. Patent Documents

Reissue of:

[64] Patent No.: 4,901,720
Issued: Feb. 20, 1990
Appl. No.: 224,301
Filed: Jul. 26, 1988

U.S. Applications:

[63] Continuation-in-part of Ser. No. 849,950, Apr. 8, 1986, Pat. No. 4,781,175.

[51] Int. Cl.[5] ..... A61B 17/39

[52] U.S. Cl. ..... 606/40; 219/121.54; 219/121.57

[58] Field of Search ..... 606/37-40; 219/121.54, 121.56, 121.57

[56] References Cited

U.S. PATENT DOCUMENTS 4,040,426 8/1977 Morrison, Jr. ..... 606/40
4,060,088 11/1977 Morrison, Jr. et al. ..... 606/40
4,188,927 2/1980 Harris .
4,209,018 6/1980 Meinke et al. .
4,271,837 6/1981 Shuler .
4,378,801 4/1983 Ooster .
4,781,175 11/1988 McGreevy et al. ..... 606/40

OTHER PUBLICATIONS

Dennis et al, "Evaluation of Electrofulguration . . . " Digestive Diseases & Sciences, vol. 24, No. 11, pp. 843-848, Nov. 1979.

*Primary Examiner*—Lee S. Cohen
*Attorney, Agent, or Firm*—John R. Ley

[57] ABSTRACT

An electrosurgical generator in an electrosurgical unit (ESU) controls the repetition rate and the energy content of bursts of RF energy delivered to a gas jet supplied by the ESU, in order to maintain RF leakage current within acceptable limits while still achieving a sufficient state of ionization in the gas jet to reliably initiate the conduction of arcs to the tissue. The repetition rate of the RF bursts is substantially reduced in an inactive state when no arcs are delivered. A relatively small number of the RF bursts delivered during the inactive state have an increased or boosted energy content to assure an adequate ionization state in the gas jet.

71 Claims, 8 Drawing Sheets

PRESETABLE DOWN COUNTER
CLK
ZD
APE
JAM INPUTS
48
4
255
CI
RST
SPE
BOOSTER GENERATOR

RF DRIVE PULSE GENERATOR
CLK Q
F-F
D R
RAMP GENERATOR
PULSE WIDTH REFERENCE CIRCUIT
ACTIVE
TARGET
BOOSTER
ANALOG SWITCH

POWER CONTROL TECHNIQUE FOR BEAM-TYPE ELECTROSURGICAL UNIT

Matter enclosed in heavy brackets [ ] appears in the original patent but forms no part of this reissue specification; matter printed in italics indicates the additions made by reissue.

CROSS-REFERENCE TO RELATED APPLICATION

This is a continuation in part of application Ser. No. 849,950, filed Apr. 8, 1986 for "Electrosurgical Conductive Gas Stream Technique of Achieving Improved Eschar for Coagulation", now U.S. Pat. No. [4,781,785] *4,781,175*, which is assigned to the assignee hereof. The disclosure of this previous application is incorporated herein by this reference.

BACKGROUND OF THE INVENTION

A concern regarding radio frequency (RF) leakage current is present in any electrosurgical unit (ESU). RF leakage current refers to the small, but nevertheless sometimes significant, current which flows into the surrounding environment from the active electrode and the conductor which supplies the active electrode, when the surgeon has activated or "keyed" the ESU prior to bringing the active electrode into operative arcing distance from the tissue of the patient. There is a concern that the RF leakage current will flow to the surgeon and to those in the operating room, exposing the surgeon and others to risk of injury. Based on these concerns, and on safety regulations, the maximum allowable amount of RF leakage current which can flow from an ESU must be controlled and limited.

The RF leakage current is at its maximum during open-circuit, full-power operating conditions. When the ESU is keyed, but no arcs travel from the active electrode to the tissue, relatively high peak-to-peak voltages of full power cause the RF leakage current to more readily disperse into the surroundings. As soon as the active electrode is brought into operative distance from the tissue, and arcs are conducted to the tissue, the circuit is closed, the output voltage drops under this "loaded" condition, and the RF leakage current is no longer of a major concern because most or all of the power is delivered to the tissue. As soon as the conductive pathways are established to the tissue, [RD] *RF* leakage current is minimized due to the considerably lower impedance path of the ionized pathways in the gas jet to the tissue. The same concern with RF leakage current also occurs after the active electrode is pulled away an inoperative distance from the tissue, but the ESU remains keyed.

Beam-type ESUs have special power requirements which other types of ESUs do not have. A beam-type ESU is one which delivers electrical energy, usually arcs, in ionized conductive pathways established in a continuously flowing jet of a predetermined gas. U.S. Pat. No. 4,781,175 (Ser. No. 849,950) discloses a beam-type ESU. In a beam-type ESU, the gas flowing past the active electrode must be maintained in an ionized state. The ionized state allows the arcs to be reliably initiated from the active electrode through the gas jet to the tissue, when the pencil-like device which delivers the gas jet and contains the active electrode is brought into an operative distance with the tissue. Without maintaining a state of sufficient ionization, arcs will not initiate when the surgeon desires, or the initiation will not be as reliable and predictable as is desired. Maintaining the ionization state in beam-type ESUs can be difficult, because the continuous flow of gas past the electrode requires electrical energy to be continually delivered in substantial magnitudes to prevent the ionized state from extinguishing.

In a conventional ESU, gas is not constantly flowing past the active electrode. Furthermore, many conventional ESUs require actual physical contact or near physical contact of the active electrode with the tissue in order to initiate the arcs. Physical contact of the active electrode to the tissue is not desirable or possible in beam-type ESUs. Therefore, the constant state of ionization in the gas jet flowing from the active electrode must not only be maintained, but it must be maintained to a degree which allows the predictable initiation of arcs in the conductive pathways established by the ionization, once the active electrode is brought into operative proximity with the tissue.

It has been determined that an effective technique of maintaining an ionized state of ionized conductive pathways in a gas is to apply relatively high peak-to-peak voltage to the gas. However, maintaining the ionization state in the gas jet of a beam-type ESU by applying a relatively high peak-to-peak voltage has the detrimental effect of increasing the RF leakage current. Thus, the requirement to maintain an effective ionized state in the gas jet sufficient to reliably initiate arcs to the tissue when desired, and the requirement to limit the amount of RF leakage current, are both significant but contradictory considerations in beam-type ESUs.

SUMMARY OF THE INVENTION

The present invention offers the capability of sustaining [and] *an* effectively ionized state of ionized conductive pathways in a gas jet of a beam-type ESU, to reliably and predictably initiate the conduction of arcs in the ionized conductive pathways when the surgeon so desires, but while doing so, limiting the RF leakage current to an acceptable level.

In accordance with the major aspects of the present invention, an electrosurgical generator means of the beam-type ESU generates bursts of radio frequency electrical energy at a predetermined repetition rate and applies those bursts to the gas jet. In an inactive operational state, when it is desired to maintain the ionized state in the gas jet without initiating or conducting arcs of electrical energy to the tissue, the generator means generates target bursts of RF electrical energy. In an active operational state when it is desired to transfer arcs in the ionized conductive pathways to the tissue, the generator means generates active bursts of RF electrical energy. The improved features of the present invention [relates to] *also relate to establishing or* changing the predetermined repetition rate of the target bursts to a value substantially less than the predetermined repetition rate of the active bursts; and during a sequence of generating a plurality of target bursts, substantially increasing the energy content of a predetermined plurality of less than all of the target bursts occurring in each sequence. The target bursts of increased energy during each sequence, known as booster target bursts, are relatively few, for example, less than ten percent. The peak-to-peak voltage of these booster target bursts is substantially higher than the voltage of the normal target bursts. The booster target bursts

[ten] *tend* to create the ionized conductive pathways, while the normal target bursts tend to sustain the ionized conductive pathways between the application of the booster target bursts.

By repeating the sequences of target bursts in the manner provided, the ionized state is effectively maintained within the gas jet. By reducing the repetition rate at which the target bursts are generated during the inactive state, the amount of RF leakage current is maintained within acceptable limits because the amount of energy delivered to the gas jet during a predetermined time period is reduced. Thus, the present invention limits the RF leakage current to an acceptable level while maintaining an effective ionized state in the gas jet to initiate arcs of electrical energy to the tissue when desired.

Because the reduced repetition rate of the target bursts may be sufficiently low to cause muscle stimulation, [the generator means also includes improved means for sensing] a condition indicative of the occurrence of arc initiation to the tissue during the inactive state *is sensed*, and thereupon [operatively changing] the repetition rate *is changed* from the lower inactive rate to the higher active rate upon sensing such a condition. As [soon as] arc initiation occurs, preferably upon occurrence of the first arc to the tissue in the inactive state, the [generator means immediately begins supplying their] higher active repetition rate *is supplied* to avoid significant muscle stimulation. In this manner, [the generator means automatically and rapidly] transitions from the inactive state to the active state *occur automatically*.

Similarly, [an effective means for terminating] the delivery of RF bursts in the active rate is [achieved] *terminated* by sensing the absence of at least one arc in the ionized conductive pathway to the tissue in the active state. Preferably, a predetermined plurality of absences of arcs are sensed before transitioning from the active state to the inactive state. The number of arc absences which occur before transitioning occurs is preferably related to the amount of power delivered during the active state. With a higher amount of active power delivered, a fewer number of arc absences must occur in the conductive pathway before transitioning from the higher active repetition rate to the lower inactive repetition rate. Conversely, with lower amount of active power delivered in the active state, more arc absences are required before [the generator means transitions] *the transition* from the higher active repetition rate to the lower inactive repetition state *occurs*.

Because the gas jet is in a highly ionized state immediately after switching from the active to the inactive state, and because the application of the booster target [pulses] *bursts* immediately after transitioning from the active to the inactive state might result in undesired arcing in the inactive state, [the generator means includes means for temporarily delivering] only normal target bursts *are delivered* for a predetermined time period after transitioning from the active to the inactive states. During this predetermined time period no booster target bursts are delivered. If the surgeon desires to immediately recommence the active state, a sufficient amount of ionization exists as a residual from the active bursts and the normal target bursts so that arc initiation can immediately and reliably occur. However, if the surgeon ceases active operation for more than the predetermined time period, for example three seconds, the booster target pulses will again commence in the sequences, to establish a sufficiently ionized state to readily support arc initiation.

Other significant advantages and improvements are available from the present invention. A more complete explanation of the details of the present invention is found in the following detailed description, taken in conjunction with the accompanying drawings. The actual scope of the present invention is defined by the appended claims.

DETAILED DESCRIPTION

Figure 1:
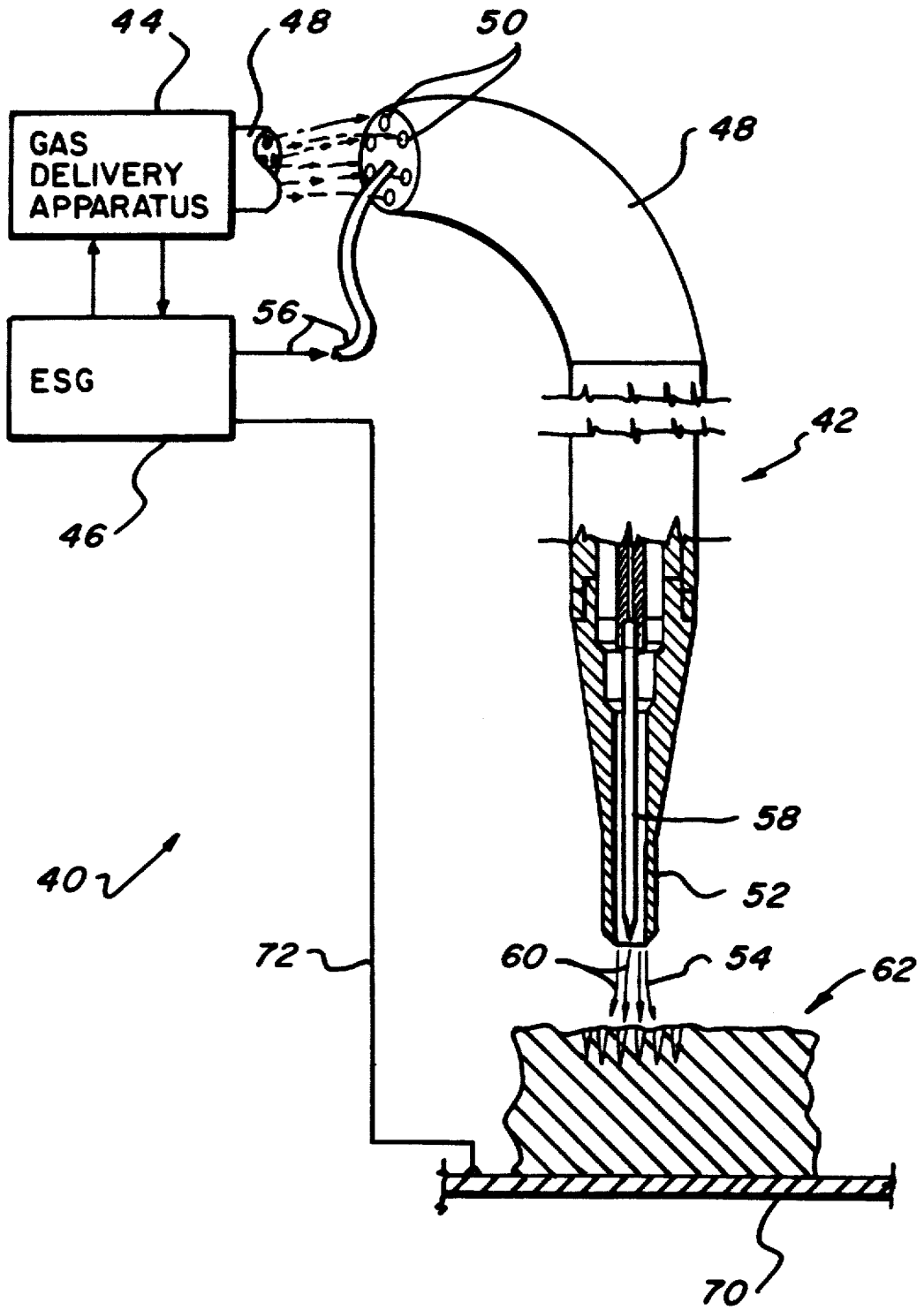
FIG. 1 is a generalized illustration of a beam-type electrosurgical unit (ESU) embodying the present invention, illustrating an electrosurgical generator means (ESG), a gas delivery apparatus, a handpiece or pencil, and a segment of patient tissue.

A beam-type electrosurgical unit (ESU) which embodies the present invention is illustrated generally in FIG. 1 and is referenced 40. The ESU 40 includes three major components, a pencil or handpiece 42 which is manipulated by the surgeon, gas delivery apparatus 44 and an electrosurgical generator means (ESG) 46. A flexible cord 48 connects the gas delivery apparatus 44 and the ESG 46 to the pencil 42. The gas delivery apparatus delivers a predetermined gas through a plurality of individual passageways or lumens 50 in the cord 48 to the pencil 42. The gas issues from a nozzle 52 of the pencil 42 in a directed or substantially laminar flow stream jet 54. The ESG 46 supplies electrical energy over a conductor 56 of the cord 48 to the pencil. The conductor 56 is electrically connected in the pencil to a needle-like electrode 58 which extends into the nozzle 52. The electrical energy supplied by the ESG 46 is of a predetermined characteristic, as discussed in greater detail below, which is sufficient to ionize the gas flowing through the nozzle 52 and to create ionized conductive pathways in the jet 54. The gas delivery apparatus 44, the cord 48 and the pencil [52] *42* are one example of means for conducting a predetermined gas in a jet. The ESG 46, the cord 48 and the electrode 58 are one example of means for transferring electrical energy in ionized conductive pathways in the gas jet.

In an active state or mode of operation of the ESU 40, electrical energy is transferred in the ionized conductive pathways in the jet 54 in the form of arcs 60. The arcs 60 travel within the jet 54 until they reach tissue 62 of the patient at the electrosurgical site. The electrical energy which is transferred into the tissue 62 creates a predetermined electrosurgical effect, usually an eschar. Details of the improved eschar available from a beam-type [ESG] *ESU* are more particularly described in the aforementioned U.S. Pat. No. 4,781,175.

The electrical energy travels through the tissue 62 to the return electrode or patient plate 70 which contacts the tissue 62. The patient plate 70 is connected by the return electrical conductor 72 to the ESG 46. A complete electrical circuit is thus established for conducting current from the ESG 46, to the electrode 58 in pencil 42, through the jet 54, to and through the tissue 62, to the patient plate 70, through the return conductor 72 and back to the ESG 46.

In an [active] *inactive* state or mode of operation of the ESU 40, an ionized state of ionized conductive pathways is maintained in the gas jet 54 issuing from the nozzle 52 but no electrical arcs are conducted in the inactive state. The ionized conductive paths create a corona or glow discharge within the jet, and the glow discharge or corona is capable of initiating arc conduction when the surgeon moves the nozzle 52 into operative proximity with the tissue 62. At this operative proximity, the ionized conductive pathways to the tissue 62 establish enough of a closed circuit through the tissue 62, a patient plate 70 and a return conductor 72, that arcs 60 commence or initiate in the jet 54.

When the surgeon activates or "keys" the ESU 40 for the delivery of the active level of electrosurgical power to the tissue, it is important that the ionized state of ionized conductive pathways within the gas jet is established. When the nozzle 52 is brought into operative proximity with the tissue 62, the ionized conductive pathways will commence conducting arcs. Upon occurrence of these arcs, the ESG 46 will automatically switch or transition from the inactive state to the active state and commence delivering an active level of power to the tissue to achieve the predetermined electrosurgical effect. Without maintaining an ionization state in the gas jet in the [inoperative] *inactive* state, it is impossible or extremely difficult to repeatedly and reliably initiate arcs 60 in the gas jet 54 to transition to the active state.

In order to achieve the electrosurgical effect, the surgeon must activate or "key" the [ESG] *ESU*. The inactive state then occurs wherein the ionized state of ionized conductive pathways in the gas jet [is] *are* created, followed by the delivery of at least one arc to the tissue while in this inactive state due to the surgeon moving the pencil into an operative distance from the tissue, followed by an automatic transition to the active state where the full [request] *requested* amount of electrosurgical power is delivered to the gas jet and conducted to the tissue.

Details of an exemplary gas delivery apparatus 44 are described in the above mentioned U.S. Pat. No. 4,781,175. Details of two types of handpieces or pencils 42 and cords 48 and associated equipment are disclosed in United States patent *application* Ser. No. 849,950 and in the U.S. patent application Ser. No. 224,485, for Electrosurgical Conductive Gas Stream Equipment, filed July 26, 1988. Additional details regarding the ESG 46 are also disclosed in U.S. Pat. *application* Ser. No. 849,950.

*The ESG 46, like the ESG described in U.S. Pat. No. 4,781,175, operates in an active operational state during which arcs of electrical energy are transferred in the ionized conductive pathways to the tissue to create a predetermined electrosurgical effect, such as the improved eschar described in U.S. Pat. No. 4,781,175, and also operates in an inactive operational state to sustain or maintain an ionized state of ionized conductive pathways to the tissue. The ionized conductive pathways in the inactive state allow initiation of the arc conduction upon a transition to the active state from the inactive state. The active state of operation of the ESG is essentially the similar to that of a conventional electrosurgical generator such as is disclosed in U.S. Pat. No. 4,429,694 as described in U.S. Pat. No. 4,781,175.*

*The inactive state of operation of the ESG 46 delivers the bursts of radio frequency energy to maintain the sustain the ionized conductive pathways in the gas jet. In the ESG 46, booster bursts and normal bursts are preferably delivered to sustain the ionization, and the booster bursts have a higher energy content than the normal bursts. A predetermined repetition rate of the bursts in the inactive state is established at a rate which is substantially less than the predetermined repetition rate of the active bursts in the active operational state. The functionality of the ESG 46 in the inactive operational state is in addition to the conventional functionality of the ESG in the active operational state. It is advantageous and preferable to combine the components of the ESG which operate in the inactive and active operational states into the single ESG 46 described.*

Figure 2:
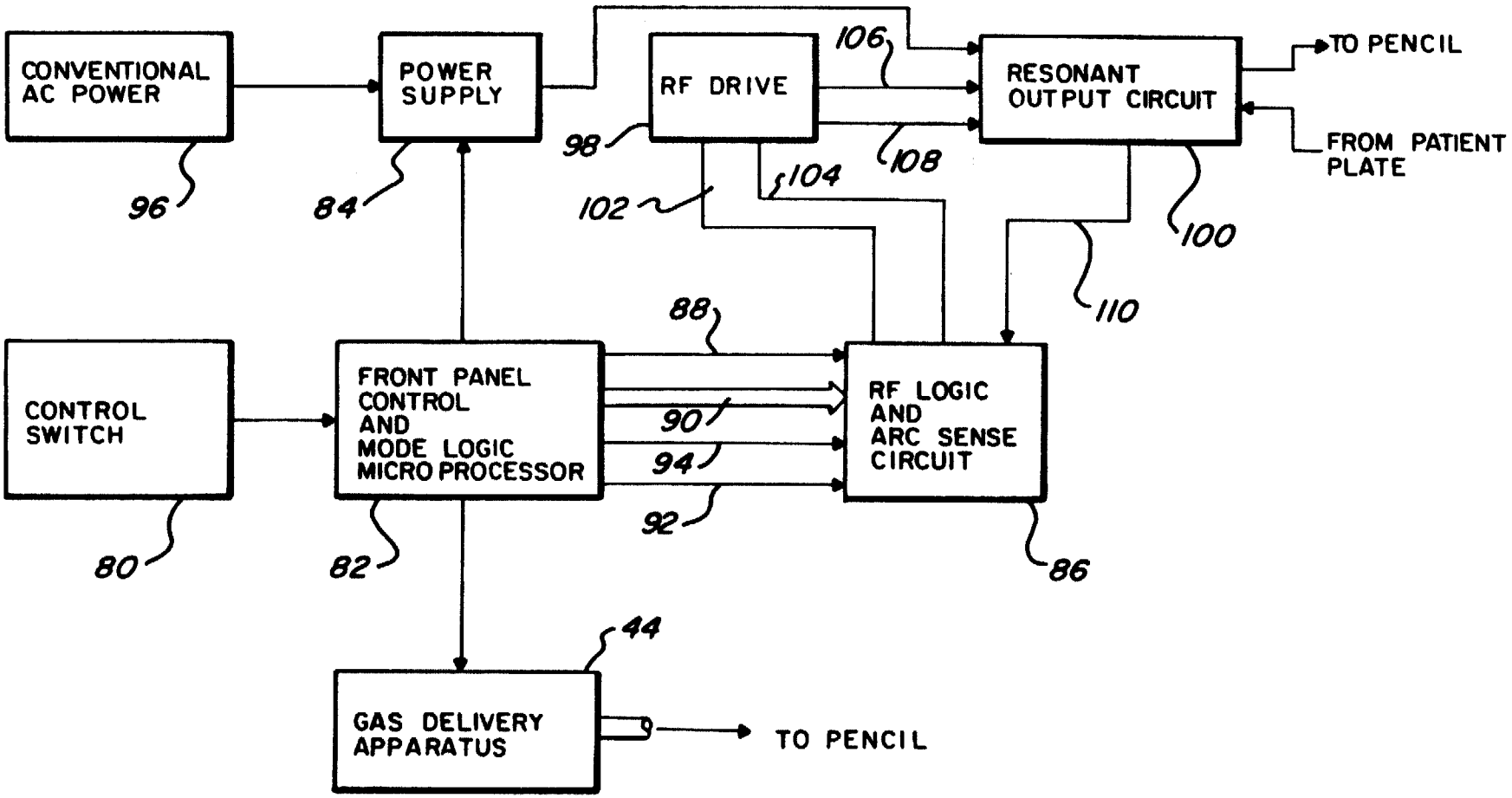
FIG. 2 is a generalized block diagram of the ESG and gas delivery apparatus shown in FIG. 1.

The major elements of an ESG 46 incorporating the present invention are illustrated in FIG. 2. A control switch 80 supplies signals to a front panel control and mode logic microprocessor circuit 82. The switch 80 controls the circuit 82 to signal the gas delivery apparatus 44 to initiate the delivery of the gas to the pencil. The switch 80 also controls the circuit 82 to signal a power supply 84 and a RF logic and arc sense circuit 86 to initiate the application of electrical energy to the gas jet.

The front panel control and mode logic microprocessor circuit 82 includes a microprocessor and various control devices, such as switches and potentiometers, which establish the selected flow rate of the gas delivered from the pencil, the source of gas to be delivered (when more than one predetermined type of gas is available), and a variety of other electrical control and operating signals, as is more fully disclosed in U.S. Pat. Ser. No. 849,950. The signals which are supplied to the RF logic and arc sense circuit 86 include a system clock signal at 88 which is derived from a microprocessor of the circuit 82, mode control and jam input count signals supplied over a data path 90 from the microprocessor to control the operation of the ESG in accordance with the type of procedure selected by the surgeon (fulguration being the primary mode relevant to this invention), an active power level analog signal at 92 which relates to the amount of electrical power selected by the surgeon for application to the tissue, and an RF enable signal at 94 which enables the RF logic and arc sense circuit 86 to function in the manner described below when electrical energy is delivered.

Gas- and electrical-related alarm conditions are also protected by the circuit 82, and the RF enable signal at 94 prevents the delivery of radio frequency electrical energy to the pencil until all of the proper operating conditions have been satisfied. A convention followed throughout this description is that the signal and the conductor upon which that signal appears will both be referenced by the same reference numeral.

The power supply 84 is activated by signals from the circuit 82. The power supply 84 receives electrical energy from conventional AC power source 96 and rectifies the AC power to DC power. When activated, the power supply 84 delivers a predetermined substantially constant voltage level of DC power to a resonant output circuit 100. The power supply 84 is conventional.

The RF logic and arc sense circuit 86 delivers drive pulse signals 102 and 104 to the RF drive 98. The drive pulse signal 102 initiates a conduction switching signal 106 from the RF drive 98, and the drive pulse signal 104 initiates an extinguishing switching signal 108 from the RF drive 98. The switching signals 106 and 108 switch energy from the power supply 84 to the resonant output circuit 100. The conduction switching signal 106 starts the flow of charging current from the power supply 84 to the resonant output circuit 100. The extinguishing switching signal 108 terminates the flow of charging current to the resonant output circuit 100. The amount of energy transferred from the power supply 84 to the output circuit 100 is determined by the time width between the drive pulse signals 102 and 104 which respectively control the switching signals 106 and 108, because the output voltage of the power supply 84 is constant. The resonant output circuit 100 commences resonating at its natural frequency (RF) after the switching signal 108 extinguishes the flow of charging current from the power supply 84.

The RF drive 98 energizes the resonant output circuit 100 at a predetermined repetition rate established by the drive signals 102 and 104, and the resonant output circuit 100 discharges at its resonant frequency by conducting electrical energy to the tissue at the surgical site. For a constant output impedance, the peak-to-peak output voltage of the resonant output circuit varies in direct relation to the width of the charging current pulse created by the switching signals 106 and 108 which are created by the drive pulse signals 102 and 104, respectively. Details regarding the RF drive 98 and resonant output circuit 100 are disclosed more completely in U.S. Pat. No. 4,429,694 and *patent application* Ser. No. 849,950.

The RF logic and arc sense circuit 86 receives a control signal 110 from the resonant output circuit 100. The control signal 110 relates to the condition of power delivery to the patient tissue, and is employed primarily to detect *or sense* the presence of arcs in the ionized conductive pathways in the gas jet to the tissue. The control signal 110 is employed by the RF logic and arc sense circuit 86 to change the repetition rate of drive signals 102 and 104 to a higher active repetition rate when electrosurgery is being performed and to a lower inactive repetition rate when the ionized state in the gas jet is to be maintained, so as to readily initiate the conduction of arcs in a reliable transition to the active state when desired.

When the pencil is not within a predetermined operative distance from the tissue, the inactive state of electrical power delivery exists. During the inactive state target bursts of RF energy are delivered to the gas jet to initiate and sustain ionization. The target bursts are of two levels: booster target bursts and normal target bursts. The booster target bursts are of higher energy content and occur much less frequently than the normal target bursts. The circuit 86 controls the energy content of the booster target bursts.

When the pencil is moved into sufficiently-close operative proximity to the tissue, an arc will travel in the ionized conductive pathway to the tissue. The control signal 110 from the resonant output circuit 100 indicates the presence of arcs. The circuit 86 [immediately] transitions from the inactive state to the active state and increases the repetition rate of the signals 102 and 104 from the inactive rate to the active rate when arcs are sensed in the inactive state.

After the pencil is removed to an inoperative distance from the tissue, the control signal 110 indicates the absence of arcs in the ionized conductive pathways to the tissue. The RF drive and arc sense circuit 86 reduces the repetition rate from the higher [arc sense circuit 86 reduces the repetition rate] *active rate to the lower inactive rate after a* predetermined number of repetitions occur when the absence of arcs is indicated.

Figure 3:
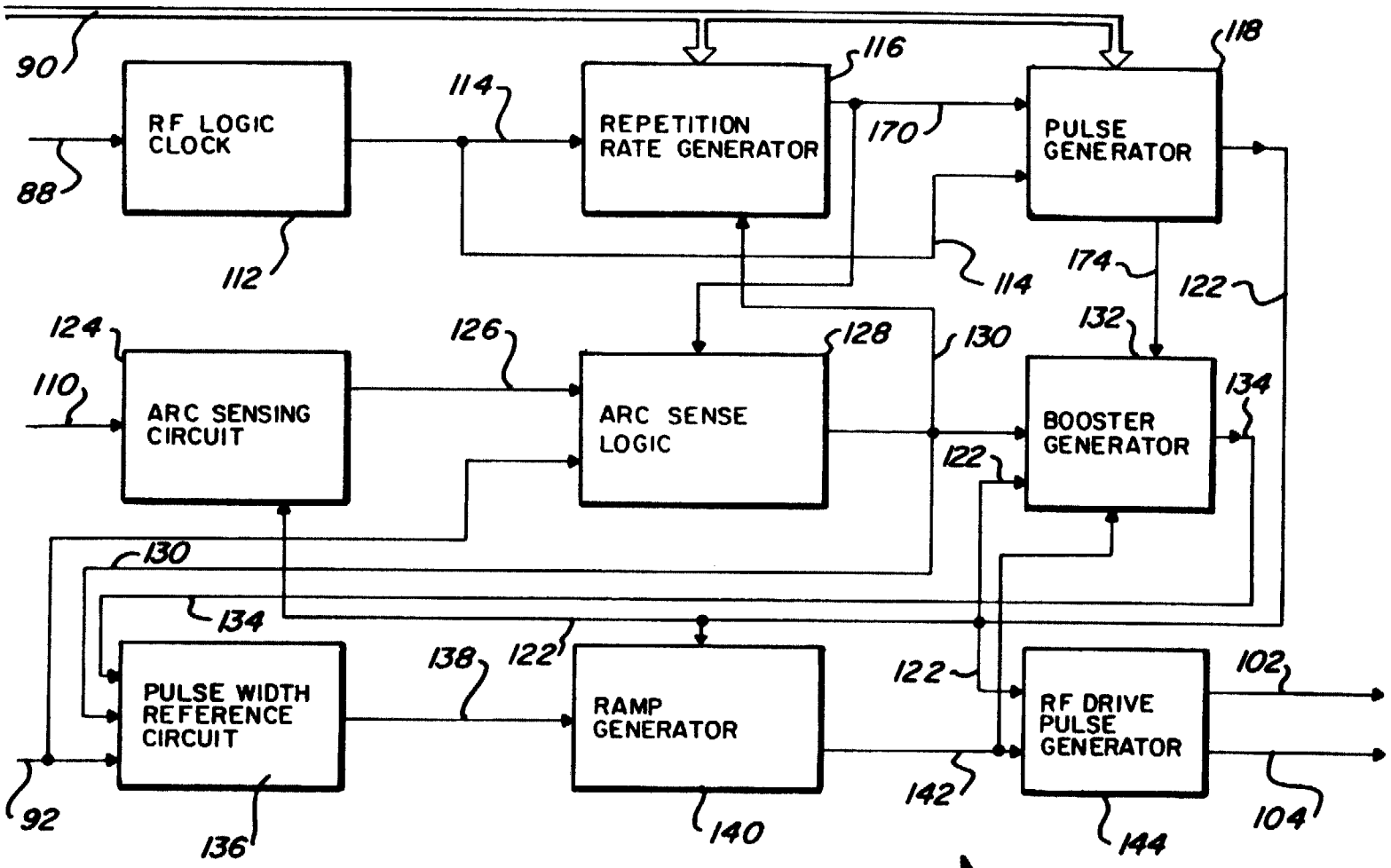
FIG. 3 is a generalized block diagram of the RF logic and arc sense circuit illustrated in FIG. 2.

Further details of the RF logic and arc sense circuit 86 are illustrated in FIG. 3. The system clock signal 88 is applied to an RF logic clock 112 which delivers clock signals 114 to a repetition rate generator 116 and to a pulse generator 118. Signals from the data path 90 are also applied to the repetition rate generator 116 and pulse generator 118. The signals from the data path 90 are derived from the microprocessor of the circuit 82 (FIG. 2) and are employed by the repetition rate generator 116 to establish the repetition rates for the active and inactive states or modes of operation pertinent to this invention. A repetition (rep) signal is applied at 170 from the repetition rate generator 116 to the pulse generator 118. The rep signal 170 establishes the repetition rate at which the pulse generator 118 supplies pulse signals 122. The width of each pulse signal 122 is established by the signals supplied by the microprocessor on the data path 90 to the pulse generator 118.

The control signal 110 from the resonant output circuit 100 (FIG. 2) is supplied to an arc sensing circuit 124. The arc sensing circuit 124 supplies a signal 126 to an arc sense logic circuit 128. The signal 126 indicates the presence or absence of arcs being delivered by the resonant output circuit 100 (FIG. 2) to the tissue. Another input signal to the arc sense logic circuit 128 is the active power level signal 92. Upon the signal 126 indicating the absence or presence of a predetermined number of arcs, as influenced by the level of the active power signal at 92, the arc sense logic 128 changes the logic level of an active/target signal 130. The active/target signal 130 is applied to the repetition rate generator 116, to a booster generator 132 and to a pulse width reference circuit 136. The active/target signal 130 controls the repetition rate generator 116 to change the repetition rate between a higher active repetition and a lower inactive repetition rate in the target state. The booster generator 132 responds to the active/target signal 130 by generating a booster signal 134 to periodically increase the energy content of a selected number of target bursts, called booster target bursts.

The active/target signal 130, the booster signal 134 and the active power level signal 92 are applied to a pulse width reference circuit 136. The pulse width reference circuit 136 responds to each of the three input signals 92, 130 and 134 by supplying a width control signal 138. A ramp generator 140 receives the pulse signal 122 and the width control signal 138, and generates a modulated width pulse signal 142. The pulse signal 122 controls the onset of the modulated width pulse signal 142, and the width control signal 138 controls and modulates the width of the pulse signal 142. An RF drive pulse generator 144 responds to the pulse signal 122 and the modulated width pulse signal 142 to create the drive pulse signals 102 and 104. Further details regarding the nature and operation of each of the elements shown in FIG. 3 are described below.

Figure 4:
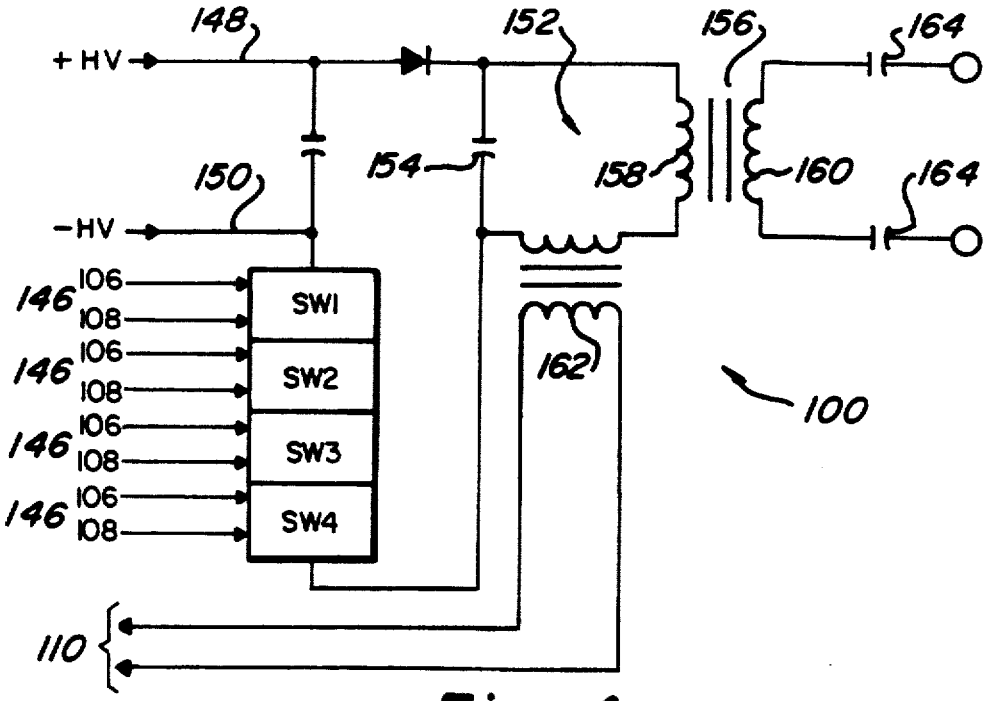
FIG. 4 is a generalized schematic diagram of the resonant output circuit shown in FIG. 2.

Details of the resonant output circuit 100 are shown in FIG. 4. Four high current switches 146 are electrically connected in series. The application of the conduction switching signal 106 causes all four high current switches 146 to become simultaneously conductive. The high voltage at terminals 148 and 150 from the power supply 84 (FIG. 2) charges a resonant LC or "tank" circuit 152 during the time the high current switches 146 are conductive. A capacitor 154 is part of the tank circuit 152 as well as an output transformer 156, having a primary winding 158 and a secondary winding 160. The primary winding 158 is thus charged with high current electrical energy from conductors 148 and 150 when the high current switches 146 are simultaneously conductive. When the high current switches 146 are extinguished or become nonconductive by the application of the extinguishing switching signal 108, the tank circuit 152 commences oscillating at its natural RF frequency. The natural frequency is primarily established by the effective inductance value of the primary winding 158 and the value of the capacitor 154. An unloaded natural frequency of approximately 500–600 KHz has proved satisfactory.

Electrical energy is transferred from the tank circuit 152 to the secondary winding 160 of the output transformer 156 and through isolating capacitors 164 to the pencil 42 and tissue 62 (FIG. 1). The impedance created within the pencil, the impedance experienced by the arcs in the ionized pathways of the gas jet, and the impedance or resistance of the tissue causes a damping effect on the electrical energy in the tank circuit 152, establishing a ring down cycle of RF oscillations. Under loaded conditions, inherent reactances in the tissue and energy delivery paths modify the unloaded frequency of the high frequency surgical signal compared to the natural frequency of the resonant circuit.

Each ring-down cycle of RF oscillations is established by one charging current pulse to the tank circuit 152. This ring-down cycle of [RD] *RF* oscillations is referred to as a "burst" of RF energy. The peak-to-peak voltage of each burst varies in direct relation to the amount or time width of the charging current pulse delivered to the tank circuit 152, for a set output impedance.

[The] *To* replenish the energy in the resonant circuit 152 after each burst or ring down cycle, the high current switches 146 are switched on and off during each repetition. These repetitions occur at a predetermined repetition rate, which is considerably less than the natural frequency of the tank circuit 152. The time during which the switches 146 are on controls the amount of energy delivered to the tank circuit 152 and also the amount of energy delivered during each burst. The resonant output circuit is thus one example of means for converting the charging pulses into RF energy bursts.

A sensing transformer 162 is also connected in series in the resonant circuit 152. The sensing transformer 162 derives the control signal 110. The control signal 110 represents the electrical signals in the tank circuit 152, and those conditions are representative of the arcing condition in the gas jet.

Figure 5:
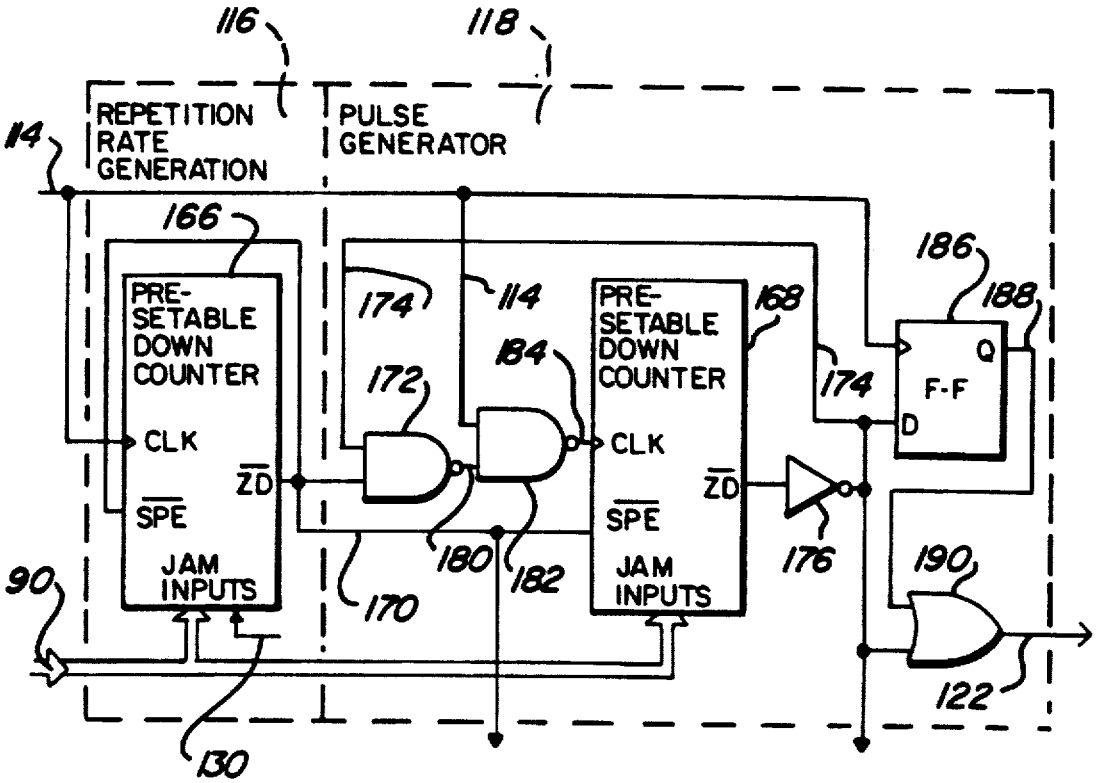
FIG. 5 is a generalized schematic and logic diagram of the repetition rate generator and the pulse generator shown in FIG. 3.
Figures 6A, 6B, 6C, 6D, 6E, 6F, 6G:
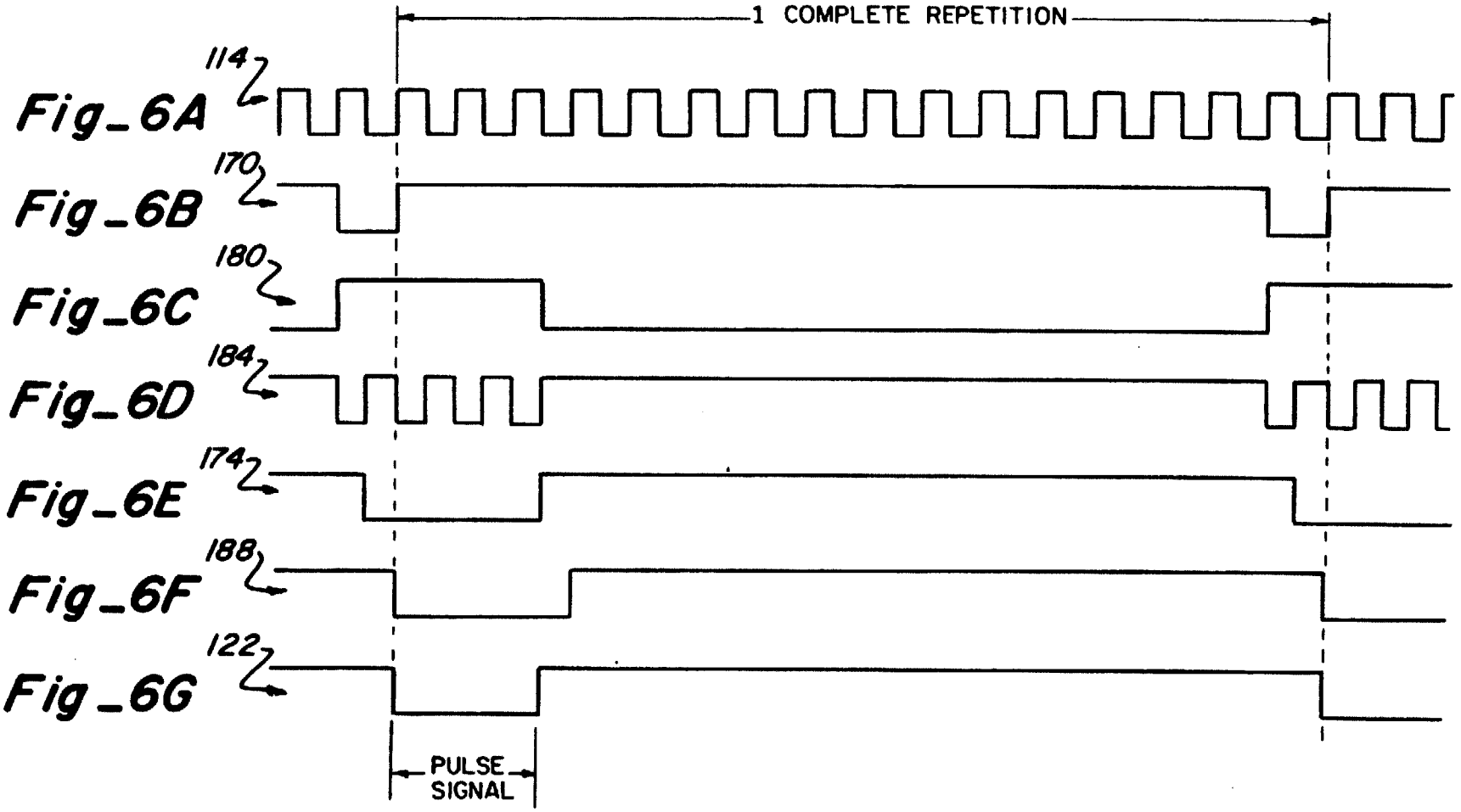
FIGS. 6A, 6B, 6C, 6D, 6E, 6F and 6G are waveform diagrams illustrating the operation of the circuit elements shown in FIG. 5.
Figure 7:
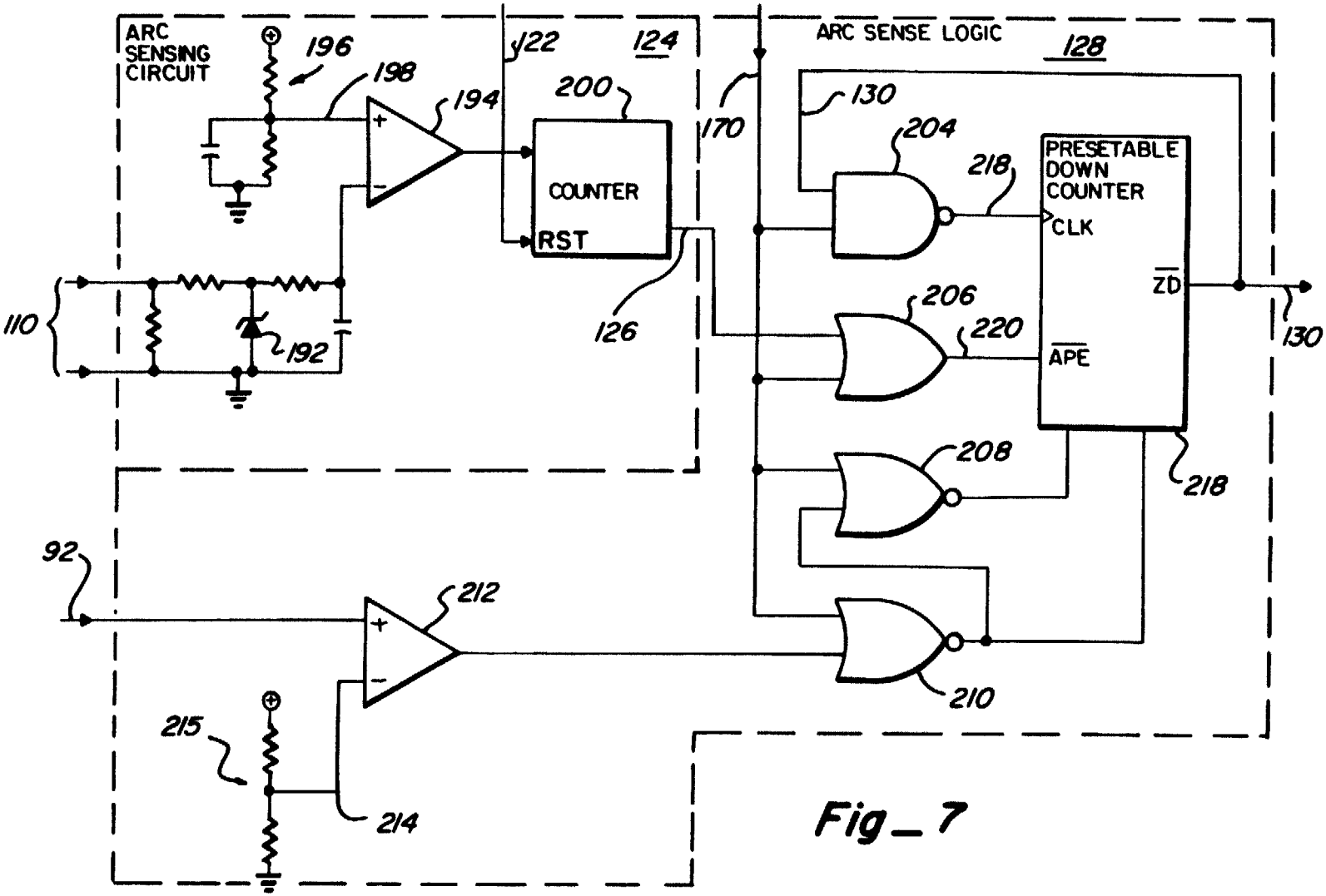
FIG. 7 is a generalized schematic and logic diagram of the arc sensing circuit and the arc sense logic shown in FIG. 3.

Details regarding the repetition rate generator 116 and the pulse generator 118 are shown in FIGS. 5 and 6A through 6G. The primary component of the repetition rate generator 116 is a presettable synchronous down counter 166. A similar down counter 168 is also the major component of the pulse generator 118. The down counters 166 and 168 are conventional items, such as those marketed under the designation CD40103B. The clock signals 114 from the RF logic clock 112 (FIG. 3) are applied to the clock inputs of both down counters 166 and 168. The clock signal 114 is illustrated in FIG. 6A. Signals from the data path 90 are applied to some of the jam input terminals of the down counter 166, and the target/active signal at 130 is applied to at least one other jam input terminal. Signals from the data path 90 are also applied to the jam input terminals of the down counter 168.

The predetermined count value of each presettable down counter is set by the signals at the jam inputs. A clock signal has the effect of decrementing the set count upon each positive transition of the clock input signal. The count which is set by the jam input signals may be established in one circumstance by the application of a low level logic signal to the synchronous preset enable (SPE) input terminal of the down counter.

The down counter 166 is the preferred form of means for establishing the repetition rate and for changing the repetition rate at which the drive pulse signals 102 and 104 (FIG. 2) are delivered to cause charging of the tank circuit 152 of the resonant output circuit 100 (FIG. 4). During the active state when an active level of power is delivered to the tissue, the active/target signal 130 is at a high level. The other signals from the data path 90 in conjunction with the high active/target signal 130, define a digital input signal which defines the jam input count to the down counter 166. The clock signals 114 decrement the down counter 166 until the count established by the jam input signals is reached, at which time the output signal 170 goes low. The signal at 170 is shown in FIG. 6B. The low signal at 170 is applied to the SPE input terminals of both down counters 166 and 168. Upon the next positive edge of a clock signal at 114, the down counters 166 and 168 are again loaded or jammed according to the counts applied at their jam input terminals.

The signal 170 establishes the length of each repetition interval in terms of the number of clock signals 114 which define each repetition. In the active state, the repetition [rate] intervals are shorter, resulting in a more frequent repetition rate. The preferred repetition interval is approximately 32 microseconds in the active state. In the inactive or target state, the repetition interval is substantially longer, occurring once each preferred time interval of approximately 56 microseconds. A lower repetition rate is thus established in the inactive state. The change in repetition rate is achieved when the active/target signal 130 changes between its high and low logic levels. A high level signal 130 changes the jam input value to shorten the repetition rate, while the low level signal 130 changes the jam input value to lengthen the repetition rate. Although FIG. 6B only illustrates the repetition rate established by the signal 170 for the active state, the inactive or target state would be similar except that the number of clock cycles 114 would be increased substantially between each low level portion of the signal 170.

The signal 170 is applied to the pulse generator 118. The count defined by the jam input signals to the counter 168 is set immediately after the signal 170 goes low. A NAND gate 172 receives the signal at 170 at one input terminal, and a signal 174 is applied to the other input terminal from an inverter 176 which is connected to the output terminal of the down counter 168. The signal 174 is illustrated in FIG. 6E. The output signal 180 from the NAND gate 172 is illustrated in FIG. 6C. The signal at 180 and the clock signal 114 are applied to the input terminals of another NAND gate 182 and the output signal 184 from the NAND gate 182 is shown in FIG. 6D. The signal 184 is applied to the clock input terminal of the down counter 168.

Upon the occurrence of a signal at 170 which establishes the length of the repetition interval relative to the clock signals 114, and hence the repetition rate, the signal 184 provided by the NAND gates 172 and 182 commences decrementing the down counter 168. The down counter 168 commences counting the number of clock pulses 114 which will establish the width of the signal 174. The down counter 168 thus becomes a preferred form of a means for generating a signal by which the pulse signal 122 will ultimately be derived. The width of the pulse signal 122 is ultimately established by the count set or jammed into the down counter 168.

The signal 174 is applied to the D input terminal of a flip-flop 186. The clock signal 114 is applied to the clock input terminal of the flip-flop 186. The output signal 188 from the flip-flop 186 is shown in FIG. 6F. The signals at 174 and 188 are applied to an OR gate 190, and the output signal from the OR gate is the pulse signal 122 which is shown in FIG. 6G. The pulse signal 122 is somewhat less in time width than the signal at 188, because of the manner in which the logic elements shown in FIG. 5 are clocked on the positive edge transitions of the clock signal 114.

Figures 8A, 8B, 8C, 8D, 8E, 8F:
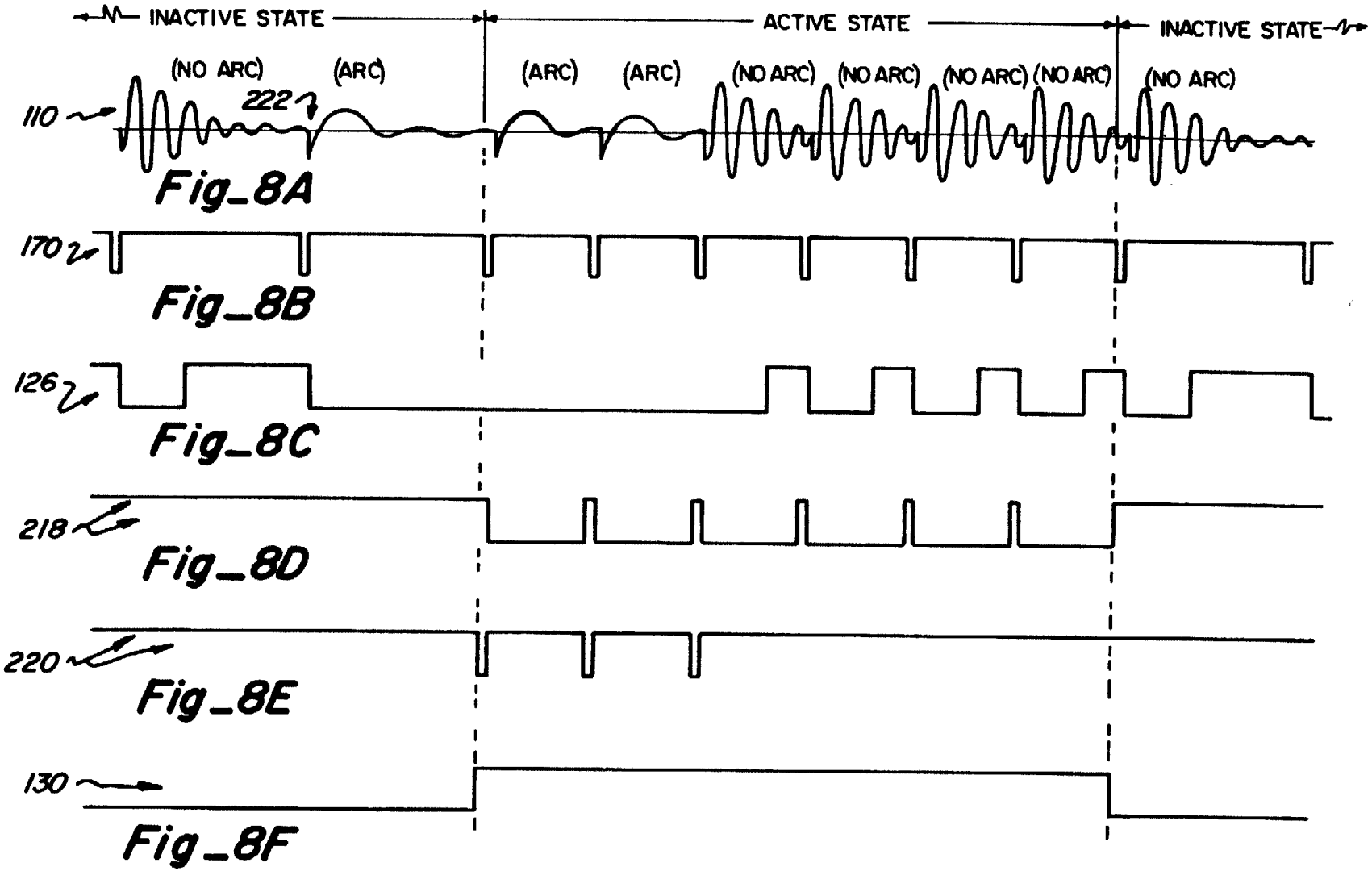
FIGS. 8A, 8B, 8C, 8D, 8E and 8F are waveform diagrams illustrating the operation of the circuit elements shown in FIG. 7 and the resonant output circuit shown in FIG. 4.

Details regarding the arc sensing circuit 124 and the arc sense logic 128 are illustrated in FIGS. 7 and 8A through 8F. The control signal 110 from the resonant output circuit 100 (FIGS. 2 and 4) is applied to the arc sensing circuit 124. This control signal 110 is illustrated in FIG. 8A. The control signal 110 is applied through resistors to a Zener diode 192. The Zener diode 192 rectifies the negative half cycles of the control signal 110 while passing the positive half cycles, which are limited by the Zener diode breakdown voltage. The signals passed by the Zener diode 192 are applied to the noninverting input of a comparator 194. A resistive network 196 establishes a threshold level 198 which is applied to the inverting input terminal of the comparator 194. Only those positive half cycles of the control signal 110 which exceed the threshold level 198 create output pulses from the comparator 194. These output pulses are applied to the clock input terminal of a conventional counter 200. Each positive half cycle of the control signal 110 which exceeds the threshold level 198 increments the counter 200.

The counter 200 supplies a high level signal 126 after it has counted a number of output pulses from the comparator 194 which correspond to the output terminal from which the signal 126 is derived. When the counter 200 reaches the predetermined output count (which is illustrated as three), the signal 126 goes high, as is shown in FIG. 8C. Thus, the arc sensing circuit 124 supplies the signal 126 only after a predetermined number of positive half cycles of the control signal 110 exceed the threshold level 198.

The predetermined number, for example three, is selected to be able to reliably distinguish an absence of arcs, because, as is illustrated in FIG. 8A, the non-arcing condition is represented by a number of oscillations after each charging repetition, while the arcing condition is represented by a highly damped signal which does not oscillate above the threshold level 198 for the required number of times before the signal 126 occurs. Thus, the arc sensing circuit 124 reliably detects arcing and non-arcing conditions from the control signal 110 and supplies the signal 126 when a non-arcing condition is detected. The signal 126 is reset to a low level at the start of each charging repetition by the application of the pulse signal 122 to the reset terminal of the counter 200.

The arc sense logic 128 receives the signal 170 from the repetition rate generator 116 (FIG. 5). The signal 170 occurs once during each repetition interval. The signal at 170 is illustrated in FIG. 8B. The signals 170 and 130 are applied to the input terminals of a NAND gate 204. The signal 170 is applied to an OR gate 206 and NOR gates 208 and 210. The signal 126 is also applied to OR gate 206. One input signal to NOR gate 208 is derived from the output signal from NOR gate 210. Another input signal to NOR gate 210 is derived from a comparator 212.

The comparator 212 receives the active power level signal 92 at its noninverting input, and a threshold level signal 214 at its inverting input. The threshold level signal 214 is established by the resistive network 215. When the active level power signal 92 exceeds the threshold signal 214, the output signal from the comparator 212 is high. For example, when the active power level signal 92 represents a value greater than approximately 85 watts, a high output signal from the comparator 212 is presented to the input terminal of the NOR gate 210. The high output signal from the comparator 212 is used for changing the jam input signals applied to a presettable down counter 216. The down counter 216 is used to establish the number of non-arcing repetition intervals which are allowed to occur prior to switching or transitioning from the active state to the inactive state. The active/target signal 130 will be held in a high level indicating an active state until a predetermined number of repetition intervals indicating an absence of arcs being delivered are sensed.

Preferably, at power levels greater than approximately 85 watts, as established by the resistive network 215, the active/target signal 130 will transition from the high active level to the low target level in approximately the preferred number of four consecutive repetition intervals when no arcs are sensed. When the active power level is less than 85 watts, the preferred number of consecutive repetition intervals which occur before transitioning to the low level active/target signal (indicating an inactive state) is preferably approximately 128.

When the ESU is first keyed, the down counter 216 is jammed to start in the inactive level with a low level signal 130 as is shown in FIG. 8F. The signals 130 and 170 cause the NAND gate 204 to supply an output signal 218 as is shown in FIG. 8D. The signal 218 forms the clock signal to the down counter 216. During the inactive state, the signal 218 remains high and therefore does not decrement the counter 216.

The signals 170 and 126 are applied to the OR gate 206, and an output signal 220 (shown in FIG. 8E) is applied to the asynchronous preset enable (APE) terminal of the down counter 216. A low signal at the APE terminal has the effect of asynchronously jamming the input count into the down counter 216. With the application of every signal 170 during the active state when the signal 126 is low, the down counter 216 is repeatedly jammed with its input count established by the output signals from the NOR gates 208 and 210. In the inactive state, when there is a high output signal [202] *126* from the counter 200, this high output signal is coupled through the OR gate 206. The high level signal 220 at the APE input terminal of the down counter 216 prevents it from being repeatedly jammed to its input count. The signals 218 are thus allowed to start decrementing the counter 216.

Operation of the arc sensing circuit 124 and the arc sense logic 128 relative to the control signal 110 and the active level power signal 92 proceeds as follows. Upon the first arcing condition in the inactive state shown at point 222 in FIG. 8A, the signal 126 from the counter 200 goes low. The absence of the signal 126 to the OR gate 206 allows the low level transition of signal 170 to create a momentary low signal at the APE input terminal of the down counter 216. The input count set by the jam input signals is thereby set in the down counter 216, and the active/target signal 130 goes high. The high active/target signal 130 allows the signal 218 from the NAND gate 204 to decrement the down counter 216. However, with each consecutive repetition interval when an arc is sensed, the signal at 220 continues to jam the input count to the down counter 216 so that the signals 218 do not effectively decrement the counter 216 because it is repeatedly rejammed. This condition continues throughout the active state while an active level of power is applied to the tissue. As soon as the pencil is pulled back away from the tissue to a predetermined distance where each repetition period results in a non-arcing condition, as is illustrated at points 224 in FIG. 8A, the counter 200 supplies a high level signal 126. The signal 126 causes the OR gate 206 to supply a high output signal 220 to the APE terminal, thereby preventing the resetting of the counter 216. The signal at 218 commences decrementing the counter, and the active/target signal 130 goes to a low level after the counter 216 has been decremented to the value established by the jam input signals from the NOR gates 208 and 210.

It is important that the repetition rate is changed from the inactive rate to the active rate immediately upon the detection of the first arc to the tissue. This is established by the signal 126 which, while creating the signal 220 to jam the inputs, causes the active/target signal 130 to immediately assume a high level. By switching immediately upon the first detected arc, the lower repetition rate of the inactive rate will have a minimum muscle stimulation effect. The inactive repetition rate is sufficiently low that it can create muscle stimulation if the change or transition to the higher active rate is not immediately accomplished.

Transition from the active state to the inactive state after a predetermined number of non-arcing repetition intervals is important to ensure that the distance at which the arcs in the gas jet extinguishes is different than the distance at which the arcs are initiated. The beam is actually a collection of individual arcs in a uniform bundle. As long as the length of the beam is such that all arcs terminate on tissue, the control signal 110 will remain heavily damped. However, as the beam is made longer with respect to the tissue, occasional arcs in the bundle fail to reach the tissue, with the result that a lightly damped control [signals] *signal* 110 occasionally occurs. Initially, the lightly damped control signal may occur only once in a large number of cycles. However, as the beam is made longer, the ratio of lightly damped to heavily damped responses increases. This reverse situation occurs when [activating the beam] *transitioning to the active state*. As the glow discharge created by the ionized gas jet is brought closer to the tissue, the glow increases until more and more arcs bridge the gap, resulting in more and more heavily damped control signals 110.

By immediately switching to the active level of delivered power upon sensing the first arc, and by not switching from the active level to the inactive level until a predetermined number of absences of arcs during sequential repetition intervals are detected, it is assured that the beam will continue in the active state even though the surgeon may unintentionally remove the pencil a short distance out of the operative range while performing the procedure. Switching to the inactive state from the active state only after a predetermined number of repetition rates assures that there will be no fluttering or other instability created by the unintentional fluctuations in position of the pencil, and also assures a more reliable and precise initiation and operation.

Figures 9, 10:
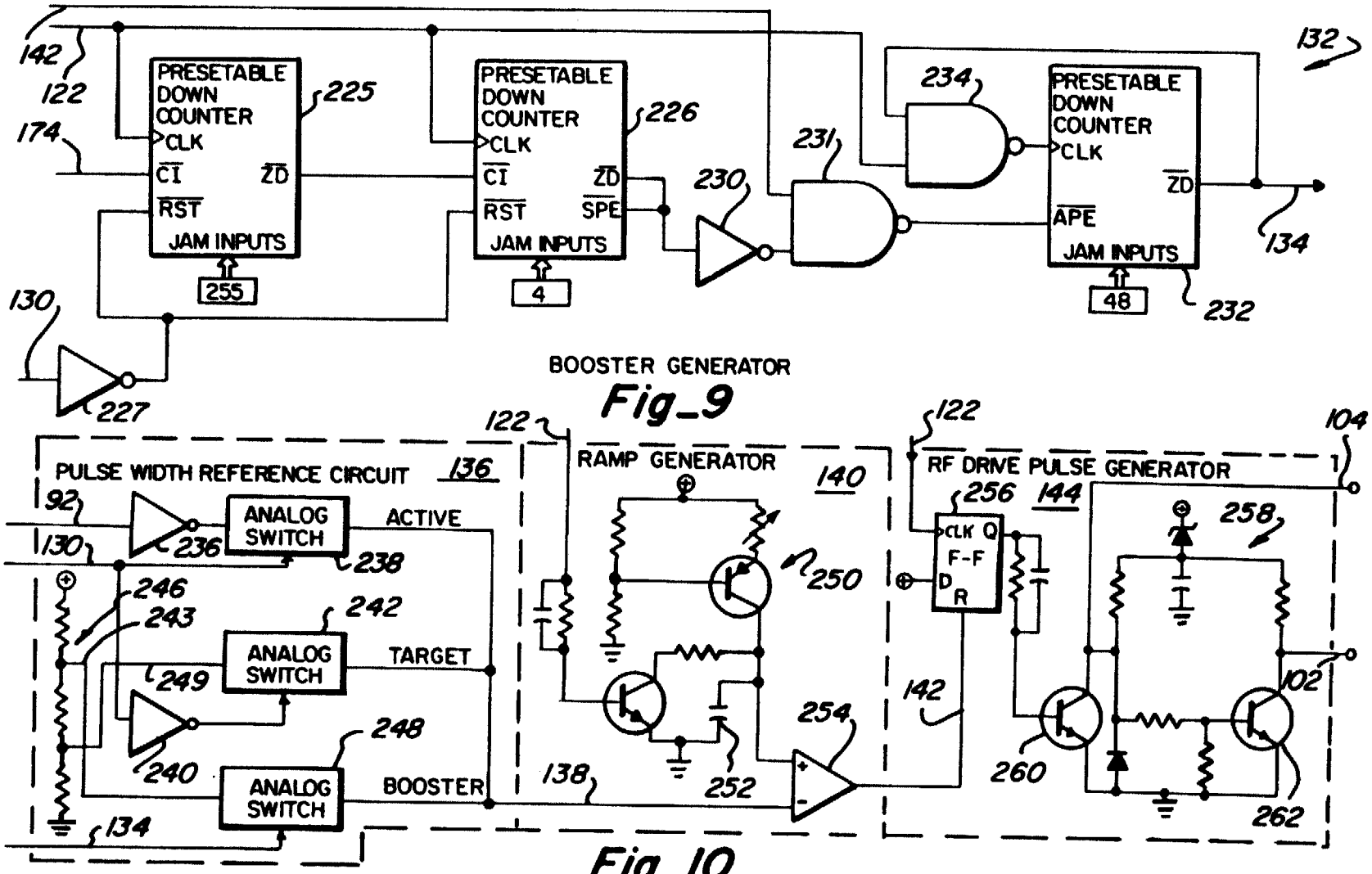
FIG. 9 is a generalized schematic and logic diagram of the booster generator shown in FIG. 3.
FIG. 10 is a generalized schematic and logic diagram of the pulse width reference circuit, the ramp generator, and the RF drive pulse generator shown in FIG. 3.

Details regarding the booster generator 132 are illustrated in FIG. 9. Two presettable down counters 225 and 226 are connected in series. The active/target signal at 130 is applied to an inverter 227. The inverter 227 supplies an output signal to the clear or reset (RST) terminals of the down counters 225 and 226. A low input signal to the RST terminals causes each down counter 225 and 226 to asynchronously be cleared and reset to its maximum count. This occurs after a transition of the active/target signal 130 to the active state, holding the counters 225 and 226 at their maximum count and therefore disabling them during the active state.

After a transition of the active/target signal 130 to the inactive state, the counters will have been set for their maximum count instead of the count normally set at the jam inputs. Since the counter 226 is normally jammed to a [counter] *count* of 4, the maximum count represents a substantial increase. Resetting the counters thus has the effect of delaying the onset of the booster signal 134, so that the added energy of the booster target pulses will not immediately cause unintentional arcing in the inactive state for a predetermined time after the active state is terminated. This is desirable because the active state has caused a residual amount of ionization which could easily support a distracting and potentially undesirable state of fluttering or intermittent arcing in the inactive state. After the predetermined time period, the residual ionization has dissipated and the fluttering condition is not likely to occur. At this point the booster signals 134 may be delivered. Resetting the counters 225 and 226 is one example of means for temporarily disabling the booster generator.

When the ESU is first keyed, the counters 225 and 226 will be jammed to their normal count, as shown in FIG. 9. The counter 225 will commence decrementing based on the pulse signal 122 from the drive pulse generator 118 (FIG. 3). The pulse signals 122 occur once each repetition period, so the down counter 225 is decremented once each repetition period.

The signal 174 is applied to a carry-in (CI) input terminal of the down counter 225. A high level signal 174 inhibits the counter 225 from counting. Thus, the application of the pulse signal 122 causes the counter 225 to be decremented only if the CI input terminal of the counter 225 is low, which will occur when the signal 174 from the pulse generator 118 (FIG. 5) goes low.

The jam input signals to the counter 225 are set for the maximum counting capability of the counter 225, which is the number [225] *255*. Once the counter 225 has been decremented, a low level output signal is supplied to the CI input terminal of the down counter 226, to allow it to commence counting. Down counter 226 decrements by one count, at which point down counter 225 again commences counting downward from its maximum count set by its jam inputs. The procedure continues until four complete cycles of counts from the counter 225 have occurred.

The output signal from the down counter 226 is applied through an inverter 230 to a NAND gate 231. The other input signal to the NAND gate 231 is the modulated width pulse signal 142 which occurs at the end of each drive pulse. Thus, at the end of the drive pulse which occurs after 1,020 repetition intervals (counted by down counters 225 and 226) the NAND gate 231 supplies a low signal to the APE input terminal of a presettable down counter 232. The jam inputs to the down counter 232 are established for a count of 48. The low signal at the APE terminal asynchronously forces the count from the jam inputs into the down counter 232. The output signal from the down counter 232, which is the booster signal 134, goes high, and the signals 122 and 134 are logically combined in the NAND gate 234 for decrementing the counter 232. After the counter 232 has counted down from its jam input count, the booster signal 134 goes low.

The booster generator 132 thus establishes a number of repetition intervals in a sequence of repetition intervals defined by the counts of the counters 225, 226 and 232. During this sequence, which in the form shown amounts to 1020 repetitions, the booster signal 134 is available to increase the energy content of 48 consecutive repetitions of target bursts. The amount of energy in these 48 target bursts, known as booster target bursts, is increased to maintain the ionization in the gas jet, while the remaining 972 repetitions in each sequence have normal level target bursts. Usually ten percent or less of the target bursts in a sequence should be booster target bursts. Preferably this percentage should be reduced to less than five percent. It has been found satisfactory to increase the energy content of the booster target bursts to three times the energy content of the normal target bursts, when about five percent of the target bursts are booster target bursts.

The width of the active level pulses, the booster target pulses and the normal target pulses is derived by the pulse width reference circuit [135] *136*, the ramp generator 140 and the RF drive pulse generator 144, the details of which are illustrated in FIG. 10.

The pulse width reference circuit 136 receives the active power level signal 92 and applies it to a buffer amplifier 236. The output signal from the amplifier 236 is applied as an analog input signal to an analog switch 238. The input control signal to the analog switch 238 is supplied by the active/target level signal 130. With a high level signal 130, the analog switch 238 applies the analog signal from the buffer amplifier 236 as the width control signal 138. When the active/target signal 130 is low, an inverter 240 supplies an input control signal to an analog switch 242. An analog input signal 249 to the analog switch 242 is derived from a resistive network 246. The control signal from the inverter 240 causes the analog switch 242 to supply the voltage level 249 as the width control signal 138. The booster signal 134 forms an input control signal for an analog switch 248. An analog input signal 243 to the analog switch 248 is also derived from the resistive network 246, and the signal 243 is a value greater than the value of the signal 249. Upon the presence of the booster signal 134, the analog switch 248 supplies the signal 243 as the pulse width control signal 138. The output signal from the analog switch 248 is greater in magnitude than that of the output signal from the analog switch 242. Arranged in this manner, it will be seen from the following description that the width or energy content of the booster target pulses is greater than the normal target pulses.

The ramp generator 140 includes a transistor circuit 250 which charges a capacitor [242] *252* in a linearly increasing or ramp fashion once the circuit 250 is triggered by a pulse signal 122 from the pulse generator 118 (FIG. 3). The linearly increasing ramp signal is applied to the noninverting input terminal of a comparator 254. The width control signal 138 is applied to the inverting input terminal of the comparator 254. When the ramp signal applied to the noninverting input terminal exceeds the analog level established by the signal 138, the modulated width output signal 142 is delivered by the ramp generator 140. The time [width] *to the occurrence* of the signal 142 created by the ramp generator 140 is determined by the analog level of the signal 138. Active pulses have a wider time width, because the output signal from the analog switch 238 will be greater in analog value. The booster target pulse will have a greater value than the normal target pulses, since the analog output signal from the analog switch 248 is greater than that of the analog switch 242. The ramp generator 140 establishes a convenient means for controlling the width of the drive pulses 102 and 104.

The RF drive pulse generator 144 includes a flip-flop 256 which is triggered by the pulse signal 122. The flip-flop 256 is reset by the modulated width pulse signal 142. A transistor circuit 258 includes a transistor 260 which is triggered into conduction by the output signal from the flip-flop 256. The output drive pulse signal 104 goes to a low level when transistor 260 commences conducting. When the output signal from the flip-flop 256 [cease] *ceases*, transistor 260 becomes nonconductive and transistor 262 becomes conductive. The drive pulse signal 104 goes high, and the drive pulse signal 102 goes low, thus terminating the width of the drive pulse delivered by the RF drive circuit 98 (FIG. 2) to the resonant output circuit 100 (FIG. 2).

The various improvements associated with the present invention have been described above. The preferred form of the present invention has been shown and described with a degree of detail. It should be understood, however, that this detailed description has been made by way of preferred example, and that the scope of the present invention is defined by the appended claims.

What is claimed:

1. In an electrosurgical unit which includes means for conducting a predetermined gas in a jet to tissue and means for transferring electrical energy in ionized conductive pathways in the gas jet, said electrical energy transferring means operatively transferring arcs to the tissue in the ionized conductive pathways in an active state to thereby create a predetermined electrosurgical effect on the tissue, said electrical energy transferring means operatively creating substantially only ionized conductive pathways in the gas jet in an inactive state to allow arc initiation upon transition to the active state, said electrical energy transferring means including electrosurgical generator means for generating target bursts of radio frequency electrical energy at a predetermined inactive repetition rate in the inactive state and for generating active bursts of radio frequency electrical energy at a predetermined active repetition rate in the active state, said electrical energy transferring means applying the bursts of radio frequency energy to the gas jet, and an improvement to said electrosurgical generator means comprising, in combination:

repetition rate changing means for changing the predetermined repetition rate of the target bursts to a value substantially less than the predetermined repetition rate of the active bursts.

2. An invention as defined in claim 1 wherein said improved generator means further comprises:

arc sensing means for sensing a condition indicative of the occurrence of an arc initiation to the tissue in ionized conductive pathways during the inactive state and for supplying an active signal upon sensing said initiation *condition*; and wherein:

said repetition rate changing means is responsive to the active signal for operatively changing the repetition rate from the inactive rate to the active rate [upon receipt of the active signal].

3. An invention as defined in claim 1 wherein said generator means further comprises:

arc sensing means for sensing a condition indicative of the absence of at least one arc in the ionized conductive pathways during the active state and for supplying a target signal upon sensing said absence *condition*; and said repetition rate changing means is responsive to the target signal for operatively changing the repetition rate from the active rate to the inactive rate [upon receipt of the target signal].

4. An invention as defined in claim 1 wherein:

the target bursts are generated in a plurality of repeating sequences during the inactive state, each sequence includes a plurality of target bursts; and said generator means further includes booster means for increasing the energy content of a predetermined plurality *of* less than all of the target bursts occurring during each sequence, those target bursts of increased energy being booster target bursts and those other target bursts being normal target bursts.

5. An invention as defined in claim 1 wherein said improved generator means further comprises:

arc sensing means for sensing a condition indicative of the occurrence of an arc initiation to the tissue in the ionized conductive pathways during the inactive state and for supplying an active signal upon sensing said initiation *condition*, said arc sensing means further sensing a condition indicative of the absence of at least one arc in the ionized pathways during the active state and for supplying a target signal upon sensing said absence *condition*; and said repetition rate changing means is responsive to the active and target signals for operatively changing the repetition rate from the inactive rate to the active rate [upon] *in response to the* receipt of the active signal and for operatively changing the repetition rate from the active rate to the inactive rate [upon] *in response to the* receipt of the target signal.

6. An invention as defined in claim 5 wherein:

the target bursts are generated in a plurality of repeating sequences during the inactive state, each sequence includes a plurality of target bursts; and said generator means further includes booster means for increasing the energy content of a predetermined plurality *of* less than all of the target bursts occurring during each sequence, those target bursts of increased energy being booster target bursts and those other target bursts being normal target bursts.

7. An invention as defined in claim 6 wherein said generator means further includes:

temporary disabling means responsive to the target signal for temporarily disabling the booster means for a predetermined disabled time period after the target signal is supplied, the target bursts applied to the gas jet during this predetermined disabled time period being normal target bursts, said temporary disabling means further responding to the expiration of the predetermined disabled time period to thereafter enable said booster means to commence operating as recited, *the predetermined disabled time period being at least the time period of one sequence of target bursts.*

8. An invention as defined in [claim] *claims* 2, 5 or 7 wherein:

said [means supplies the active signal upon sensing] *initiation condition is* the first arc to the tissue occurring while in the inactive state.

9. An invention as defined in claims 3, 5 or 7 wherein:

said [arc sensing means supplies the target signal upon sensing] *absence condition is* the absence of a predetermined plurality of consecutive arcs in the active state.

10. An invention as defined in claim 9 wherein:

said generator means further includes means for establishing a predetermined active power level of electrical energy to be delivered to the gas jet in the active state; and said arc sensing means is also responsive to the predetermined active power level and operatively supplies the target signal upon the absence of a relatively fewer predetermined plurality of consecutive arcs when the predetermined active power level is relatively higher and supplies the target signal upon the absence of a relatively greater predetermined plurality of consecutive arcs when the active power level is relatively lower.

11. An invention as defined in claims 4 or 6 wherein:

the booster target bursts are consecutive in each sequence.

12. An invention as defined in claim 11 wherein the number of booster target bursts in each sequence is in a range of less than ten percent of the total number of target bursts in each sequence.

13. An invention as defined in claims 4 or 6 wherein:

the booster target bursts have an energy content established at least in part by a [peak to peak] *peak-to-peak* voltage of at least one cycle of the radio frequency electrical energy of each booster target bursts; and the [peak to peak] *peak-to-peak* voltage of at least one cycle of each booster target burst is substantially greater than the [peak to peak] *peak-to-peak* voltage of any cycle of each normal target burst.

14. An invention as defined in claim 7 wherein said generator means further comprises:

drive pulse generator means for generating driving pulses of energy having time width durations corresponding to the amount of energy contained in each pulse, said drive pulse generator means also generating the driving pulses at repetition rates corresponding to the repetition rates of the bursts;

drive means receptive of the [drive] *driving* pulses and operative for creating charging pulses having a time width related to the [drive] *driving* pulses;

conversion means receptive of each charging pulse and operative for converting each charging pulse into one said radio frequency burst, each burst having an energy content which relates to the energy content of the corresponding charging pulse which created the burst; and pulse width adjusting means connected to said drive pulse generator means and operative for adjusting the width of driving pulses which control the charging pulses that established the booster target bursts and the normal target bursts to achieve the recited energy characteristics of the target bursts in the active and inactive states.

15. An invention as defined in claims 1, 4 or 6 wherein said repetition rate changing means establishes a substantially constant repetition rate in the inactive state and a different substantially constant repetition rate in the active state.

16. In an electrosurgical unit which includes means for conducting a predetermined gas in a jet to tissue and means for transferring electrical energy in ionized conductive pathways in the gas jet, said electrical energy transferring means operatively transferring arcs to the tissue in the ionized conductive pathways in an active state to thereby create a predetermined electrosurgical effect on the tissue, said electrical energy transferring means operatively creating substantially only ionized conductive pathways in the gas jet in an inactive state to allow arc initiation upon transition to the active state, said electrical energy transferring means including electrosurgical generator means for generating target bursts of radio frequency electrical energy at a predetermined repetition rate in the inactive state and for generating active bursts of radio frequency electrical energy at a predetermined repetition rate in the active state, said electrical energy transferring means applying the bursts of radio frequency energy to the gas jet, and an improvement to said electrosurgical generator means comprising, in combination:

means for generating the target bursts in a plurality of repeating sequences during the inactive state, each sequence including a plurality of target bursts; and booster means for substantially increasing the energy content of a predetermined plurality *of* less than all of the target bursts occurring during each sequence, those target bursts of increased energy being booster target bursts and those other target bursts being normal target bursts.

17. An invention as defined in claim 16 wherein the number of booster target bursts in each sequence is in a range of less than ten percent of the total number of target bursts in each sequence.

18. An invention as defined in claim 17 wherein:

the booster target [busts] *bursts* are consecutive in each sequence.

19. An invention as defined in claim 17 wherein:

the energy content of the booster target bursts is approximately three times the energy content of the normal target burst.

20. An invention as defined in claim 19 wherein the number of target bursts in each sequence is approximately [less than] five percent of the total number of target bursts in each sequence.

21. An invention as defined in claim 16 wherein said booster means further comprises:

means for delaying the application of booster target bursts for a predetermined time after said generator means transitions from delivering active bursts to delivering *normal* target bursts.

*22. A method of operating an electrosurgical unit for conducting electrosurgery on tissue, comprising:*

*conducting a predetermined gas in a jet to tissue;*

*transferring electrical energy to the gas jet in an active state by generating active bursts of radio frequency electrical energy occurring at a predetermined active repetition rate to create arcs in ionized conductive pathways in the gas jet and to transfer arcs in the ionized conductive pathways to the tissue for achieving a predetermined electrosurgical effect on the tissue;*

*transferring electrical energy to the gas jet in an inactive state by generating target bursts of radio frequency electrical energy occurring at a predetermined inactive repetition rate to create substantially only ionized conductive pathways in the gas jet which allow arc initiation upon transition to the active state; and*

*establishing the predetermined inactive repetition rate of the target bursts at a predetermined value which is substantially less than the predetermined active repetition rate of the active bursts.*

*23. A method as defined in claim 22 further comprising:*

*sensing a condition indicative of the occurrence of arc initiation to the tissue in ionized conductive pathways during the inactive state; and*

*terminating the predetermined inactive repetition rate of the target bursts in response to the sensed initiation condition.*

*24. A method as defined in claim 23 wherein the sensed initiation condition is the first arc initiated to the tissue in the inactive state.*

*25. A method as defined in claim 22 further comprising:*

*sensing a condition indicative of the absence of at least one arc in the ionized conductive pathways during the active state; and*

*establishing the predetermined inactive repetition rate of the target bursts in response to the sensed absence condition.*

*26. A method as defined in claim 25 wherein the sensed absence condition is the absence of a predetermined plurality of consecutive arcs in the active state.*

*27. A method as defined in claim 22 further comprising:*

*sensing a condition indicative of the occurrence of an arc initiation to the tissue in the ionized conductive pathways during the inactive state;*

*establishing the active repetition rate in response to the sensed initiation condition;*

*sensing a condition indicative of the absence of at least one arc in the ionized pathways during the active state; and*

*establishing the inactive repetition rate in response to the sensed absence condition.*

*28. A method as defined in claim 27 wherein the sensed absence condition is the absence of a predetermined plurality of consecutive arcs in the active state.*

*29. A method as defined in claim 28 wherein the sensed initiation condition is the first arc initiated to the tissue during the inactive state.*

*30. A method as defined in claim 27 further comprising:*

*generating target bursts in a plurality of repeating sequences during the inactive state, each sequence including a plurality of target bursts; and*

*increasing the energy content of a predetermined plurality of less than all of the target bursts occurring during each sequence, those target bursts of increased energy being booster target bursts and those other target bursts being normal target bursts.*

*31. A method as defined in claim 30 further comprising:*

*temporarily ceasing the generation of booster target bursts for a predetermined disabled time period upon sensing the absence condition, the predetermined disabled time period being at least the time period of one sequence; and*

*beginning the generation of booster target bursts after the expiration of the predetermined disabled time period.*

*32. A method as defined in claim 31 wherein the sensed absence condition is the absence of a predetermined plurality of consecutive arcs in the active state.*

*33. A method as defined in claim 31 further comprising:*

*sensing a predetermined active power level of electrical energy delivered to the gas jet in the active state;*

*establishing the inactive repetition rate in response to sensing the absence of a relatively fewer predetermined plurality of consecutive arcs when the predetermined active power level is relatively higher; and*

*establishing the inactive repetition rate in response to sensing the absence of a relatively greater predetermined plurality of consecutive arcs when the predetermined active power level is relatively lower.*

*34. A method as defined in claim 33 further comprising:*

*consecutively generating the booster target bursts in each sequence.*

*35. A method as defined in claim 34 further comprising:*

*generating a number of booster target bursts in each sequence in a range of less than ten percent of the total number of target bursts in each sequence.*

*36. A method as defined in claim 27 further comprising:*

*generating target bursts in a plurality of repeating sequences during the inactive state, each sequence including a plurality of target bursts; and*

*increasing the energy content of a predetermined plurality of less than all of the target bursts occurring during each sequence, those target bursts of increased energy being booster target bursts and those other target bursts being normal target bursts.*

*37. A method as defined in claim 36 further comprising:*

*sensing a condition indicative of the absence of at least one arc in the ionized conductive pathways during the active state;*

*temporarily ceasing the generation of booster target bursts for a predetermined disabled time period upon sensing the absence condition, the predetermined disabled time period being at least the time period of one sequence; and*

*beginning the generation of booster target bursts after the expiration of the predetermined disabled time period.*

*38. A method as defined in claim 37 wherein the sensed absence condition is the absence of a predetermined plurality of consecutive arcs in the active state.*

*39. A method as defined in claim 37 further comprising:*

*sensing a predetermined active power level of electrical energy delivered to the gas jet in the active state;*

*establishing the inactive repetition rate in response to sensing the absence of a relatively fewer predetermined plurality of consecutive arcs when the predetermined active power level is relatively higher; and*

*establishing the inactive repetition rate in response to sensing the absence of a relatively greater predetermined plurality of consecutive arcs when the predetermined active power level is relatively lower.*

*40. A method as defined in claim 36 further comprising:*

*generating a number of booster target bursts in each sequence in a range of less than ten percent of the total number of target bursts in each sequence.*

*41. A method as defined in claim 36 further comprising:*

*generating a number of booster target bursts in each sequence at approximately five percent of the total number of target bursts in each sequence; and*

*increasing the energy content of the booster target bursts to a value approximately three times greater than the energy content of the normal target bursts.*

*42. A method of operating an electrosurgical unit for conducting electrosurgery on tissue, comprising:*

*conducting a predetermined gas in a jet to tissue;*

*transferring electrical energy to the gas jet in an active state by generating active bursts of radio frequency electrical energy occurring at a predetermined active repetition rate to create the arcs in ionized conductive pathways in the gas jet and to transfer arcs in the ionized conductive pathways to the tissue for achieving a predetermined electrosurgical effect on the tissue;*

*transferring electrical energy to the gas jet in an inactive state by generating target bursts of radio frequency electrical energy occurring at a predetermined inactive repetition rate to create substantially only ionized conductive pathways in the gas jet which allow arc initiation upon transition to the active state, the target bursts occurring in a plurality of repeating sequences and each sequence including a plurality of target bursts; and*

*increasing the energy content of a predetermined plurality of less than all of the target bursts occurring during each sequence, those target bursts of increased energy being booster target bursts and those other target bursts being normal target bursts.*

*43. A method as defined in claim 42 further comprising:*

*generating a number of booster target bursts in each sequence in a range of less than ten percent of the total number of target bursts in each sequence.*

*44. A method as defined in claim 43 further comprising:*

*consecutively generating the booster target bursts in each sequence.*

*45. A method as defined in claim 43 further comprising:*

*increasing the energy content of the booster target bursts to a value approximately three times greater than the energy content of the normal target bursts.*

*46. A method as defined in claim 45 further comprising:*

*generating a number of booster target bursts in each sequence at approximately five percent of the total number of target bursts in each sequence.*

*47. A method as defined in claim 42 further comprising:*

*delaying the generation of booster target bursts for a predetermined time after ceasing the delivery of active bursts and commencing the delivery of normal target bursts.*

*48. An electrosurgical generator for an electrosurgical unit which includes means for conducting a predetermined gas in a jet to tissue and means for transferring arcs of*

*electrical energy in ionized conductive pathways in the gas jet in an active state to create a predetermined electrosurgical effect on the tissue, the arcs in the active state resulting from bursts of radio frequency electrical energy occurring at a predetermined active repetition rate; said electrosurgical generator comprising:*

*burst generator means operative during an inactive state for generating bursts of radio frequency electrical energy to create substantially only ionized conductive pathways in the gas jet to allow arc initiation in the gas jet upon transition from the inactive state to the active state, the inactive state occurring other than during the occurrence of the active state; and*

*repetition rate establishing means for controlling the burst generator means to establish a repetition rate of the bursts in the inactive state which is substantially less than the predetermined repetition rate of the bursts during the active state.*

*49. An electrosurgical generator as defined in claim 48 further comprising:*

*arc sensing means for sensing a condition indicative of the occurrence of an arc initiation to the tissue in ionized conductive pathways during the inactive state and for supplying an active signal upon sensing said initiation condition; and wherein:*

*said repetition rate establishing means is responsive to the active signal for operatively terminating the predetermined inactive repetition rate.*

*50. An electrosurgical generator as defined in claim 49 wherein:*

*said initiation condition is the first arc to the tissue occurring while in the inactive state.*

*51. An electrosurgical generator as defined in claim 48 further comprising:*

*arc sensing means for sensing a condition indicative of the absence of at least one arc in the ionized conductive pathways during the active state and for supplying a target signal upon sensing said absence condition; and*

*said repetition rate establishing means is responsive to the target signal for establishing the predetermined inactive repetition rate.*

*52. An electrosurgical generator as defined in claim 51 wherein:*

*said absence condition is the absence of a predetermined plurality of consecutive arcs in the active state.*

*53. An electrosurgical generator as defined in claim 48 further comprising:*

*arc sensing means for sensing a condition indicative of the occurrence of an arc initiation to the tissue in the ionized conductive pathways during the inactive state and for supplying an active signal upon sensing said initiation condition, and further sensing a condition indicative of the absence of at least one arc in the ionized pathways during the active state and for supplying a target signal upon sensing said absence condition; and*

*said repetition rate establishing means is responsive to the active and target signals for operatively terminating the predetermined inactive repetition rate in response to the active signal and for operatively establishing the predetermined inactive repetition rate in response to the target signal.*

*54. An electrosurgical generator as defined in claim 53 wherein:*

*said absence condition is the absence of a predetermined plurality of consecutive arcs in the active state.*

*55. An electrosurgical generator as defined in claim 54 wherein:*

*said initiation condition is the first arc to the tissue occurring while in the inactive state.*

*56. An electrosurgical generator as defined in claim 53 wherein:*

*said burst generator means generates target bursts in a plurality of repeating sequences during the inactive state, each sequence includes a plurality of target bursts; and said burst generator means further includes:*

*booster means for increasing the energy content of a predetermined plurality of less than all of the target bursts occurring during each sequence, those target bursts of increased energy being booster target bursts and those other target bursts being normal target bursts.*

*57. An electrosurgical generator as defined in claim 56 wherein said burst generator means further includes:*

*temporary disabling means responsive to the target signal for temporarily disabling the booster means for a predetermined disabled time period after the target signal is supplied, the predetermined disabled time period being at least the time period of one sequence of target bursts; and*

*reenabling means responsive to the expiration of the predetermined disabled time period for thereafter enabling said booster means to commence operating as recited.*

*58. An electrosurgical generator as defined in claim 57 wherein:*

*said absence condition is the absence of a predetermined plurality of consecutive arcs in the active state.*

*59. An electrosurgical generator as defined in claim 57 wherein:*

*said arc sensing means is further responsive to a predetermined active power level of electrical energy delivered to the gas jet in the active state and operatively supplies the target signal upon the absence of a relatively fewer predetermined plurality of consecutive arcs when the predetermined active power level is relatively higher and supplies the target signal upon the absence of a relatively greater predetermined plurality of consecutive arcs when the active power level is relatively lower.*

*60. An electrosurgical generator as defined in claim 59 wherein:*

*the booster target bursts are consecutive in each sequence.*

*61. An electrosurgical generator as defined in claim 60 wherein the number of booster target bursts in each sequence is in a range of less than ten percent of the total number of target bursts in each sequence.*

*62. An electrosurgical generator as defined in claim 48 wherein:*

*the burst generator means generates target bursts in a plurality of repeating sequences during the inactive state, each sequence includes a plurality of target bursts; and said target burst generator means further includes:*

*booster means for increasing the energy content of a predetermined plurality of less than all of the target bursts occurring during each sequence, those target bursts of increased energy being booster target bursts and those other target bursts being normal target bursts.*

*63. An electrosurgical generator as defined in claim 62 further comprising:*

*arc sensing means for sensing a condition indicative of the absence of at least one arc in the ionized conductive pathways during the active state and for supplying a target signal upon sensing said absence condition; and wherein said burst generator means further includes:*

*temporary disabling means responsive to the target signal for temporarily disabling the booster means for a predetermined disabled time period after the target signal is supplied upon sensing the absence condition, the predetermined disabled time period being at least the time period of one sequence; and*

*reenabling means responsive to the expiration of the predetermined disabled time period for thereafter enabling said booster means to commence operating as recited.*

*64. An electrosurgical generator as defined in claim 63 wherein:*

*said absence condition is the absence of a predetermined plurality of consecutive arcs in the active state.*

*65. An electrosurgical generator as defined in claim 63 wherein:*

*said arc sensing means is further responsive to a predetermined active power level of electrical energy delivered to the gas jet in the active state and operatively supplies the target signal upon the absence of a relatively fewer predetermined plurality of consecutive arcs when the predetermined active power level is relatively higher and supplies the target signal upon the absence of a relatively greater predetermined plurality of consecutive arcs when the active power level is relatively lower.*

*66. An electrosurgical generator for an electrosurgical unit which includes means for conducting a predetermined gas in a jet to tissue and means for transferring arcs of electrical energy in ionized conductive pathways in the gas jet in an active state to create a predetermined electrosurgical effect on the tissue, the arcs in the active state resulting from bursts of radio frequency electrical energy occurring at a predetermined active repetition rate; said electrosurgical generator comprising:*

*burst generator means for generating a plurality of repeating sequences of bursts of radio frequency electrical energy during an inactive state to create substantially only ionized conductive pathways in the gas jet to allow arc initiation in the gas jet upon transition from the inactive state to the active state, each sequence including a plurality of bursts; and*

*booster means for increasing the energy content of a predetermined plurality of less than all of the bursts occurring during each sequence in the inactive state, those bursts of increased energy during the inactive state being booster target bursts and those other bursts being normal target bursts.*

*67. An electrosurgical generator as defined in claim 66 wherein the number of booster target bursts in each sequence is in a range of less than ten percent of the total number of target bursts in each sequence.*

*68. An electrosurgical generator as defined in claim 67 wherein:*

*the booster target bursts are consecutive in each sequence.*

*69. An electrosurgical generator as defined in claim 67 wherein:*

*the energy content of the booster target bursts is approximately three times the energy content of the normal target bursts.*

*70. An electrosurgical generator as defined in claim 69 wherein the number of booster bursts in each sequence is approximately five percent of the total number of bursts in each sequence.*

*71. An electrosurgical generator as defined in claim 66 wherein said booster means further comprises:*

*means for delaying the application of booster target bursts for a predetermined time after the transition from the delivery of active bursts to the delivery of normal target bursts.*

* * * * *